United States Patent
Romanini et al.

(10) Patent No.: US 6,504,145 B1
(45) Date of Patent: Jan. 7, 2003

(54) METHOD OF EXCITATION OF AN OPTICAL CAVITY FOR DETECTING GAS TRACES

(75) Inventors: Daniele Romanini, Grenoble (FR); Alexandre Katchanov, Saint Martin d'Heres (FR)

(73) Assignee: Universite Joseph Fourier, Grenolble Cedex (FR)

( * ) Notice: Subject to any disclaimer, the term of this patent is extended or adjusted under 35 U.S.C. 154(b) by 0 days.

(21) Appl. No.: 09/674,627

(22) PCT Filed: Apr. 30, 1999

(86) PCT No.: PCT/FR99/01030
§ 371 (c)(1),
(2), (4) Date: Oct. 30, 2000

(87) PCT Pub. No.: WO99/57542
PCT Pub. Date: Nov. 11, 1999

(30) Foreign Application Priority Data

Apr. 30, 1998 (FR) .............................................. 98 05753

(51) Int. Cl.[7] .............................................. G01N 21/25
(52) U.S. Cl. .................................. 250/227.23; 356/437
(58) Field of Search ........................... 250/227.23, 343, 250/339.13, 339.12, 221, 222.1, 222.2; 356/436, 437, 439, 440

(56) References Cited

U.S. PATENT DOCUMENTS

| | | | |
|---|---|---|---|
| 4,793,709 A | 12/1988 | Jabr et al. ................... 356/445 |
| 5,026,991 A | 6/1991 | Goldstein et al. ........... 250/343 |
| 5,432,610 A | * 7/1995 | King et al. .................. 356/432 |
| 5,528,040 A | * 6/1996 | Lehman ....................... 250/343 |
| 5,912,740 A | * 6/1999 | Zare et al. ................... 356/437 |

* cited by examiner

Primary Examiner—Robert H. Kim
Assistant Examiner—Chih-Cheng Glen Kao
(74) Attorney, Agent, or Firm—Duane Morris LLP

(57) ABSTRACT

The invention concerns a method for detecting gas traces with a semiconductor laser coupled with an optical resonant cavity containing a species to be analyzed. The laser is coupled with the cavity so that the light is not projected back towards the laser when the cavity is in resonance mode. The laser supplies an amplified and fine-tuned emission on the re-injected frequency and, when a current pulse is applied thereon, its frequency moves from a predetermined initial frequency to a final predetermined frequency. The laser is excited by a first current pulse such that its frequency is sequentially locked on the cavity successive modes. The luminous intensity decreasing time in the cavity is measured at the end of the pulse and the excitation and measurement steps are repeated for successive current pulses, to cover a spectral range to be analyzed.

8 Claims, 4 Drawing Sheets

METHOD OF EXCITATION OF AN OPTICAL CAVITY FOR DETECTING GAS TRACES

BACKGROUND OF THE INVENTION

1. Field of the Invention

The present invention relates to the detection of gas traces. It more specifically relates to the cavity ring down spectroscopy (CRDS) method.

2. Description of the Related Art

The major principles of the CRDS method will be reminded in relation with FIG. 1. The method consists of emitting light from a laser 1 in a resonant optical cavity 2. An optical isolation system or a deflector 3 is used to avoid feedback effects of the resonant cavity on the laser. The light coming out of the resonant cavity is received by a photodetector 4 and is sent to an analyzer 5. Assuming that photons have been injected into cavity 2, once the injection of photons into the cavity by the laser is interrupted, for example, by cutting off the laser or by reflecting its beam, the photons remain trapped in the cavity and decrease exponentially along time. If the cavity is empty, or for a wavelength that does not correspond to an absorption line of a gas contained in the cavity, this decrease will exhibit a certain time constant essentially determined by the mirror losses at the considered wavelength. If the cavity contains a chemical species having an absorption line at the wavelength of the injected photons, this time constant will be reduced.

This is illustrated in FIG. 2, which shows the intensity collected by photodetector 4 as a function of time. It is assumed that at time T0, the excitation is interrupted and that there exists a given density of photons $I_0$ in the cavity. If the cavity contains no absorbing species at the considered frequency, the fall time has a first value t1. If the cavity contains absorbing species, the fall time becomes t2. The concentration of absorbing species in the cavity is related to the difference t2−t1.

Many studies and laboratory experiments have been carried out to use and improve this gaseous species detection method. It has quickly been understood that, to turn laboratory experiments into a method likely to be implemented by an industrial device at low cost, a continuous laser had to be used.

The first experiments on the CRDS method have been carried out with pulsed lasers providing very intense power pulses with a relatively wide spectrum. A sufficient number of photons could then be injected into the cavity to perform measurements. However, this method would come up against the major disadvantage of the complexity and cost of pulsed lasers. On the other hand, it has long since been suggested (see D. Z. Anderson et al., Applied Optics, Volume 23, 1984, p. 1238–1245) to use a continuous laser as a source. All these known techniques are discussed in detail in U.S. Pat. No. 5,528,040 of K. K. Lehmann filed in 1994, which also advocates the use of a continuous laser as a source.

As experiments have advanced, one of the major problems to be solved has appeared to be the injection of a sufficient amount of light into the resonant cavity.

Another problem that is posed by prior art devices is the fact that they are generally complex since they include control systems to set the laser frequency at the time of interruption of the laser/cavity coupling.

BRIEF SUMMARY OF THE INVENTION

Thus, an object of the present invention is to provide a method for measuring traces of a chemical species by the use of a resonant cavity spectroscopy method in which the injection of photons into the resonant cavity from a continuous laser is optimized.

Another object of the present invention is to provide a method that is easy to implement due to its providing no frequency control of the system.

To achieve these objects, the present invention provides a method of gas trace detection by a laser coupled to a resonant optical cavity containing a chemical species to be analyzed, including the steps of providing that the coupling between the laser and the cavity is such that the light is only sent back to the laser when the cavity is in a resonance mode and at the resonance frequency; providing a semiconductor laser of a type adapted to providing an emission amplified and thinned down at the reinjected frequency, and such that, when a current rectangular pulse is applied thereto, its frequency moves from a determined initial frequency to a determined final frequency; exciting the laser by a first current rectangular pulse so that the laser frequency sequentially locks on successive modes of the cavity; measuring the fall time of the light intensity in the cavity at the end of said rectangular pulse; and repeating the steps of excitation and measurement for successive current rectangular pulses, to cover a spectral range to be analyzed.

According to an embodiment of the present invention, the laser is a laser diode.

According to an embodiment of the present invention, the laser is excited by sequential current rectangular pulses of increasing intensity.

According to an embodiment of the present invention, the laser is excited by sequential current rectangular pulses of increasing length.

According to an embodiment of the present invention, the laser is excited by identical sequential current rectangular pulses, the temperature at which the laser is stabilized being incremented after each rectangular pulse.

According to an embodiment of the present invention, the cavity is of V-shaped type, comprised of a first oblique mirror with respect to the direction of incidence of the laser, a second mirror orthogonal to the direction of incidence of the laser, and a third mirror forming a cavity with the first two mirrors.

According to an embodiment of the present invention, the cavity is a conventional cavity with two mirrors and a polarizing isolator is arranged between the laser and the cavity to prevent the returning to the laser of a direct reflection on the rear surface of the entrance mirror and to transmit to the laser a radiation having undergone a resonance in the cavity.

According to an embodiment of the present invention, the cavity is set to operate in a mode close to a degenerated mode, the secondary transverse modes being all gathered on a same side of a main corresponding transverse mode, the laser performing a scanning in the direction starting from the side opposite to that where the secondary lateral modes are found.

The foregoing objects, features and advantages of the present invention will be discussed in detail in the following non-limiting description of specific embodiments in connection with the accompanying drawings.

DETAILED DESCRIPTION OF THE INVENTION

Before describing the present invention, the applicant insists on reminding that, in the field of optical spectroscopy, terms such as "thin Line", "monomode system", etc. often have different meanings according to authors. The vocabulary which will be used in relation with FIGS. 3A to 3C will thus be clarified hereafter.

Generally speaking, in techniques of gaseous species detection by optical absorption measurement, it is analyzed whether a specific absorption line of the considered species is present or not and its intensity is attempted to be determined.

Figure 1:
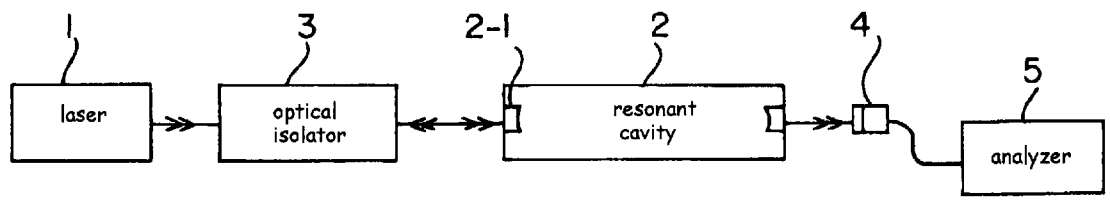
FIG. 1 shows the general diagram of a device implementing the CRDS method.
Figure 2:
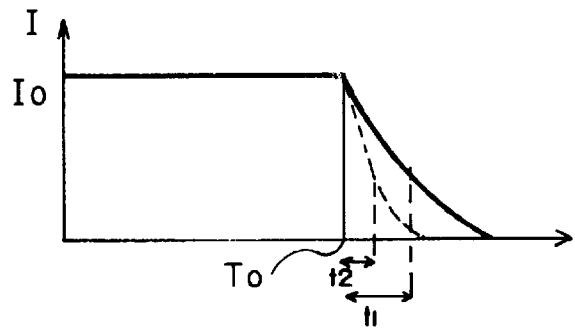
FIG. 2 shows intensity-vs.-time curves characterizing the attenuation of photons trapped in a cavity.
Figure 3A:
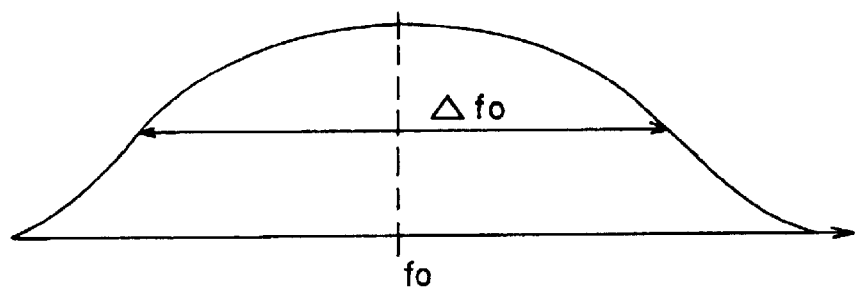
FIGS. 3A to 3C show curves of the spectral intensity versus the frequency, respectively for an absorption line, for a laser line, and for longitudinal modes of a cavity.

FIG. 3A shows the intensity of an absorption line versus frequency. The line has a central frequency f0 and a width $\Delta f0$. As an example, the 1651-nm absorption line of methane has an absorption line width $\Delta f0=4.4$ GHz (which corresponds to a wavelength range of 0.04 nm).

Figure 3B:
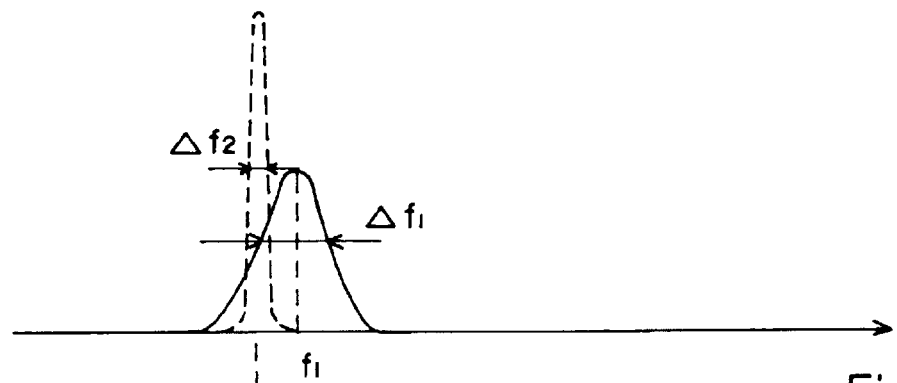

A continuous laser such as a laser diode or another semiconductor laser of adjustable frequency will emit a line f1 of width $\Delta f1$ such as shown in FIG. 3B. Generally speaking, $\Delta f1$ will be much smaller than width $\Delta f0$ of the absorption line, and this will always be the case herein.

Figure 3C:
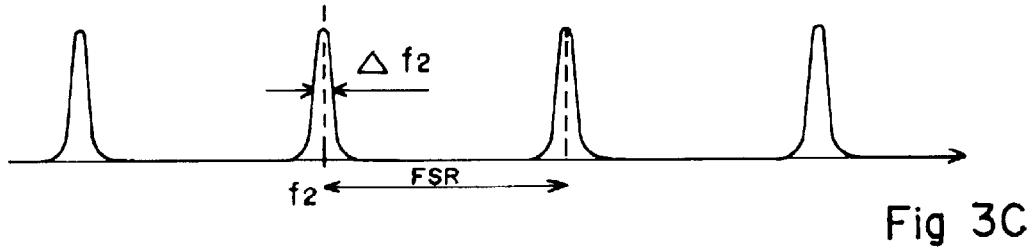

Further, as illustrated in FIG. 3C, a resonant optical cavity of given length can resonate on one or the other of several frequencies or longitudinal modes spaced apart by a distance or free spectral range FSR. To simplify the discussion, the frequency of a cavity mode will be called f2, noting that a frequency f2+kFSR where k is a positive integer, negative or null, should be considered. For each of the longitudinal modes, the possible resonance width $\Delta f2$ is very small, that is, it is small as compared to the width of laser line $\Delta f1$, which is itself small as compared to the width of absorption line $\Delta f0$. The case, which is frequent in practice, where $\Delta f1$ is smaller than the FSR distance between modes of the cavity will be considered. For example, FSR may be equal to 300 MHz (approximately 10 times less than the width of the absorption line to be studied).

As shown in FIG. 3B, the power of the laser line is distributed over width $\Delta f1$ and only the portion of this power of width $\Delta f2$ corresponding to the width of a cavity mode can be injected into the cavity. It can thus be seen that the amount of photons injected into the cavity is small as compared to the total intensity of a laser line. The power stored by the cavity will thus be small, and all the smaller as the intensity of a continuous laser of diode or semiconductor type is generally small. Further, this intensity will fluctuate according to the relative centering of central emission frequency f1 of the laser and to the frequency of a neighboring mode f2 of the cavity. Now, what can be detected on photodetector 4 directly depends on the number of photons that will have been injected into the cavity.

According to a first feature of the present invention, the resonant cavity is used as the source of a positive optical feedback to the laser, which is chosen to be of a type strongly responding to an optical feedback.

Figure 4A:
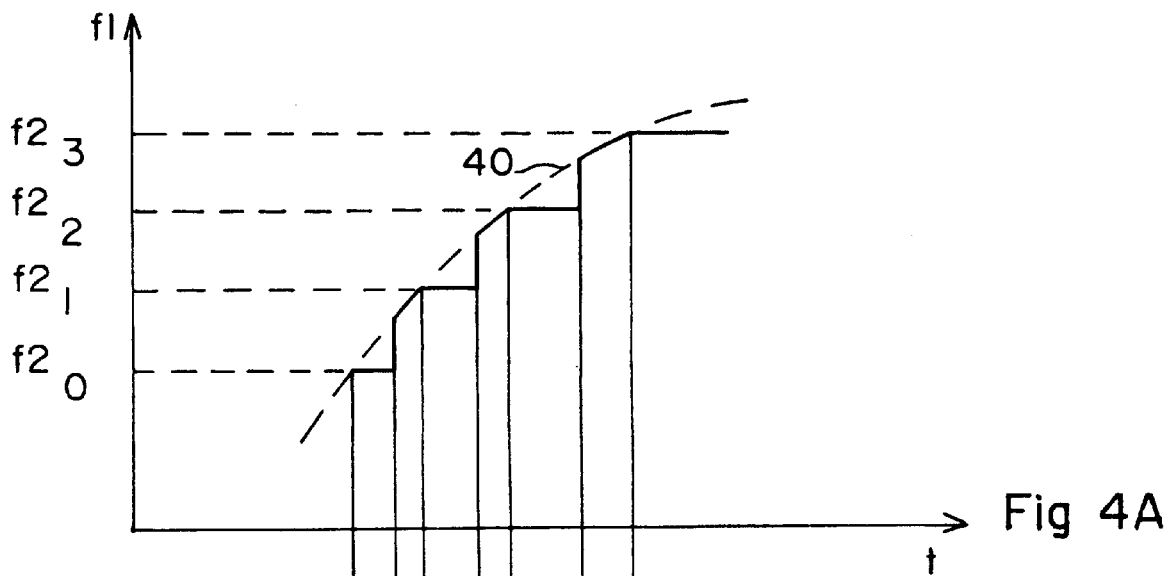
FIGS. 4A and 4B show curves characterizing the synchronization between a laser and a cavity.
Figure 4B:
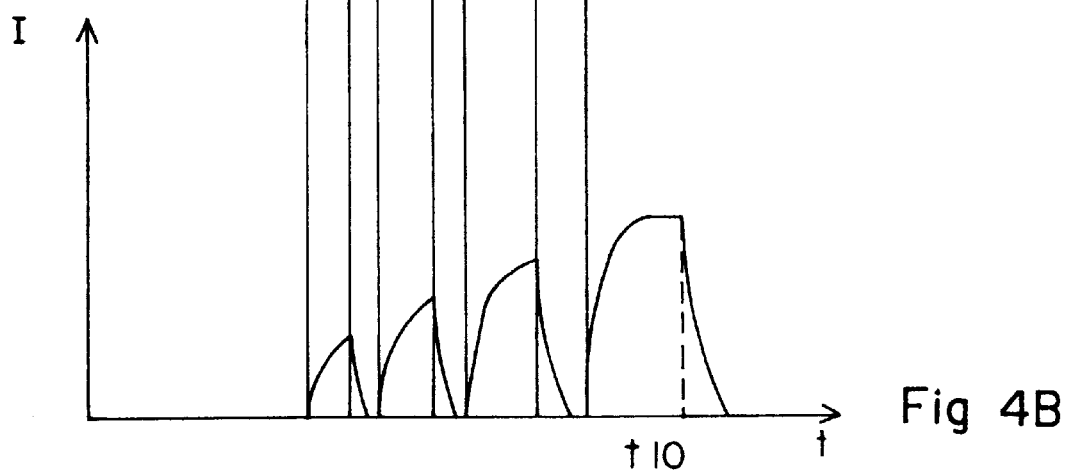

To have this optical feedback phenomenon understood, it should be reminded that the resonant cavity, to be efficient as regards the absorption detection, must have highly-reflective mirrors, for example mirrors with a reflection coefficient close to 99.998. Thus, when the laser sends light onto entrance mirror 2-1 of the resonant cavity, this light is mostly sent back onto the laser. This is likely to disturb the laser. Therefore, in conventional assemblies, an optical isolator is used between the laser and the cavity. In the context of the present invention, an assembly adapted to selectively sending back onto the laser a waveband of a width corresponding to the width of a cavity mode for a resonance frequency of the cavity is used. If the laser emits power around frequency f1, and if the laser line contains power at a frequency f2, the cavity starts resonating and only the waves corresponding to this resonance frequency are sent back onto the laser. If the laser is a laser with a strong length will tend to lock on the considered frequency. Thus, the cavity transmission is such as shown in FIGS. 4A–4B, that is, the cavity transmits for each lock-up frequency $f2_0$, $f2_1$, $f2_2$, $f2_3$. If the laser supply is abruptly interrupted, at a time t10, said laser stops emitting and a damping phenomenon is observed, which is attempted to be studied after time t10.

According to a second feature of the present invention, a laser, for example a semiconductor diode continuous laser, is used such that, when supplied by a constant current rectangular pulse, its wavelength progressively increases from an initial value. More specifically, a temperature-stabilized laser is chosen which, at the end of a current rectangular pulse of determined duration, is at a determined final frequency, this final frequency depending on the duration and on the amplitude of the current, without it being necessary to provide a control loop. However, as previously indicated, given the coupling between the laser and the cavity, it can be considered that the laser frequency successively shifts fran the frequency of one cavity mode to the frequency of the next mode. An initial setting of the laser such that its initial wavelength is close to and slightly smaller than that of the absorption line which is desired to be studied will of course be chosen (a close but slightly greater frequency).

Thus, normally, when a current rectangular pulse is applied to the laser as shown by the curve in dotted lines 40 of FIG. 4A, the wavelength emitted by the laser tends to progressively increase (in FIG. 4A, f1 designates a wavelength and not a frequency). As indicated, due to the coupling with the cavity, for each of the natural frequencies or frequencies of the longitudinal modes of the cavity $f2_0$, $f2_1$, $f2_2$, $f2_3$, the laser wavelength will tend to lock on the considered frequency. Thus, the cavity transmission is such as shown in FIGS. 4A–4B, that is, the cavity transmits for each lock-up frequency $f2_0$, $f2_1$, $f2_2$, $f2_3$. If the laser supply is abruptly interrupted, at a time t10, said laser stops emitting and a damping phenomenon is observed, which is attempted to be studied after time t10.

A measurement has thus been obtained for a point of the absorption band. This measurement could possibly be repeated several times. Then, a measurement for another point of the absorption band will be performed again, while making sure that the laser interruption is ensured for another cavity mode. This can be ensured in various ways, for example by increasing the intensity of the current rectangular pulse applied to the laser, by increasing the duration of the rectangular pulse, or by modifying the laser temperature to modify its initial oscillation frequency. A succession of points enabling restoring the shape of the absorption band to be studied could thus be obtained.

An advantage of the present invention is the fact that a very large measurement stability can be obtained, since the setting of the cavity is not modified from one measurement to the other, only the laser excitation being changed and, as known, a laser such as a semiconductor laser, for example a laser diode, can be regulated in an extremely reliable manner. It can thus be ensured, for example, that measurement points are regularly spaced apart (plus or minus a free spectral range).

Figure 5:
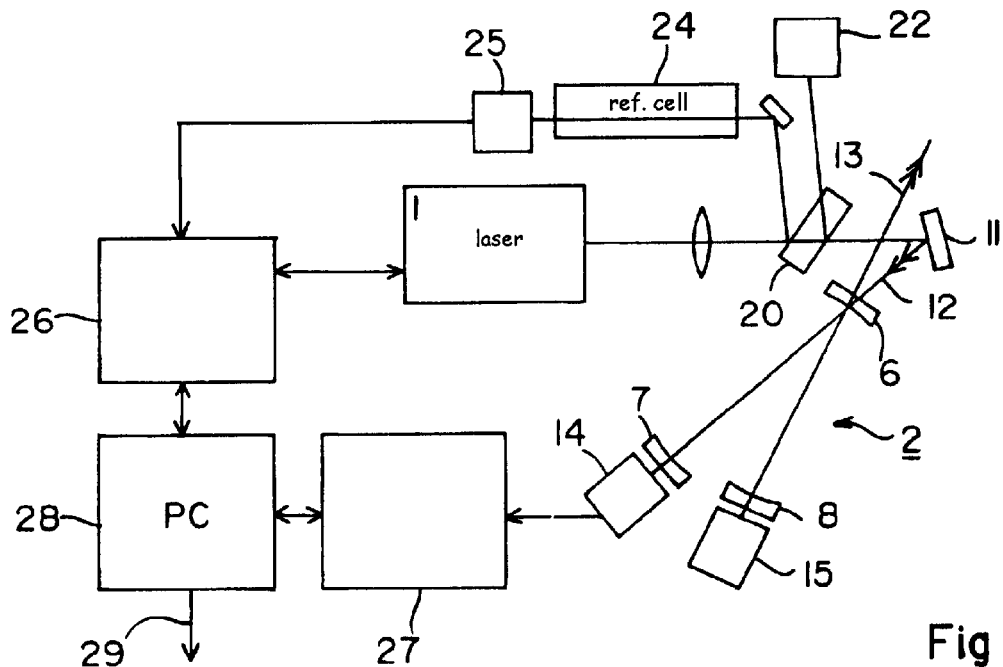
FIG. 5 shows a specific embodiment of a device according to the present invention.
Figure 6:
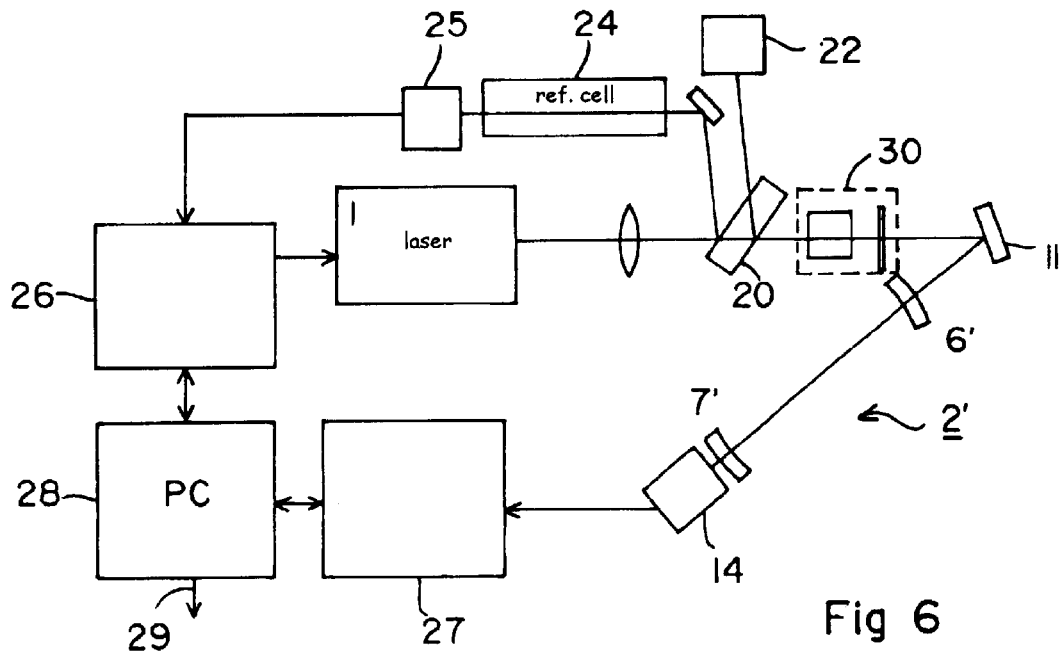
FIG. 6 shows another specific embodiment of a device according to the present invention.

Examples of devices implementing the present invention are illustrated in FIGS. 5 and 6.

In FIG. 5, the laser is designated again with reference 1. Cavity 2 is a V-shaped cavity comprised of an input mirror 6 and mirrors 7 and 8 arranged substantially in the shown manner to form a resonant cavity. Thus, the direct beam sent by the laser is reflected by a mirror 11 towards the rear surface of a first mirror 6 and towards a second mirror 7. The light reflected by mirror 7 is sent back by the front surface of mirror 6 to a mirror 8. When the cavity is not tuned, the general beam sent by the laser and arriving on the rear surface of mirror 6 by an optical path 12 is sent back according to a beam 13 which is not directed to return to the laser. The direct beam arriving on mirror 7 is sent onto mirror 6. However, its intensity as it exits mirror 6 is extremely low since it undergoes the double transmission attenuation of mirror 6 and can be considered as negligible as long as cavity 2 is not tuned. The intensity sent back onto optical path 12 only becomes significant when the tuning wavelength of the cavity (f2 in FIG. 3C) is sent by the laser. The feedback and line thinning phenomenon then occurs. A maximum injection then occurs in the cavity. By exciting the laser with a current rectangular pulse of given characteristics, the variation described in relation with FIGS. 4A and 4B is obtained. At the end of the current rectangular pulse, the output of a photodetector 14 or 15, arranged for example behind one of mirrors 7 or 8, may be analyzed to study the optical decrease phenomenon associated with the presence or the absence of an absorption line of a species searched in the cavity.

Further, FIG. 5 shows various conventional means, known in prior devices. In particular, a separator 20 may be used to deflect a first portion of the beam towards a photodetector 22. A second portion of the laser beam could be deflected towards a reference cell 24 containing the chemical species of which the presence is desired to be detected. This reference cell is associated with a detector 25, the output of which may be sent back to a system 26 for setting laser 1 to enable its initial setting. The output of detector 14 arranged behind mirror 7 is for example sent to a digitizing circuit 27, the output of which is sent to a properly programmed processor 28, associated with an output 29 of information provision and also acting upon the laser scanning to fulfil various requirements.

FIG. 6 shows, as an example, an alternative embodiment of the present invention in which same elements as in FIG. 5 are designated by same references. In this embodiment, resonant cavity 2' is a conventional cavity formed of two opposite mirrors 6' and 7'. All the power sent to the rear surface of mirror 6' is transmitted back to laser 1. To avoid this, an optical isolator 30, for example a rectilinear polarizer followed by a quarter wave plate are arranged between the laser and the cavity. However, this optical isolator is an isolator responsive to polarization. It is assumed that the laser sends a wave of given polarizing and that the corresponding polarizing wave sent back by mirror 6' is blocked by isolator 30. However, when cavity 2 starts resonating, the wave transmitted back at frequency $f_2$ (see FIG. 3C) is depolarized with respect to the initial incident wave and crosses back isolator 30 with a small attenuation. It is thus sent back onto laser 1 and the previously-described feedback effect occurs, and a tuning of the laser on frequency $f_2$ and a thinning down of the laser emission line are obtained again.

Means for calculating the value of the concentration of a searched gas based on the values of the fall rates measured at various points of the absorption line are known and will not be described in further detail herein. The corresponding calculations will for example be performed by processor 28 of FIGS. 5 and 6.

Further, in a known manner, the distance between the laser and the cavity influences the feedback. To overcome this effect, either a control may be provided, or this path may be made to oscillate, for example by a vibration source, to excite a continuous sequence of modes when the laser is scanned.

Influence of the Transverse Cavity Modes

In the foregoing description, and more specifically in FIG. 3C, the cavity has been shown to have resonance modes at frequencies f2 separated from one another by an interval equal to free spectral range FSR of the cavity. This is a simplification. Indeed, a cavity is likely to resonate on several transverse electromagnetic modes (TEM), generally designated as $TEM_{ij}$. To each of these modes actually corresponds a geometric shape of the light spot on the mirrors. This means in the case of what has been previously described that the laser is likely to lock on one or the other of the lateral cavity modes or simultaneously on several modes. The relation between the fall time in the presence of a gas and the fall time in the absence of any gas is then less precise since it cannot be sure that the two fall times have been measured for same lateral modes. Indeed, for a given cavity, the fall time constant somewhat depends on the lateral mode TEM of the cavity that has been excited. This is due in particular to the fact that these modes correspond to distinct geometric shapes of the light spots. Different portions of the mirrors are lit in the different lateral modes and the fall times depend on the small uncontrollable local variations of the reflective factors of the mirrors.

Figure 7A:
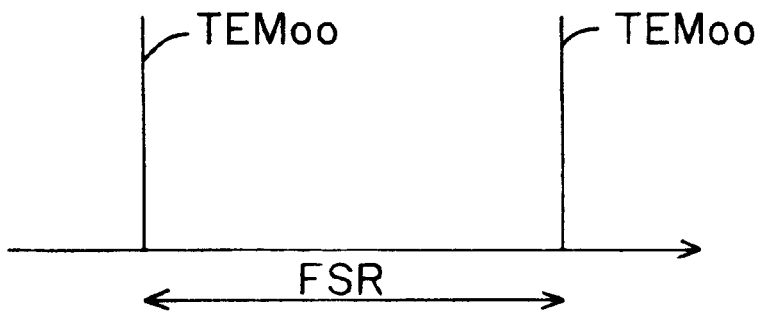
FIGS. 7A to 7D illustrate the lateral modes for various types of cavities.
Figure 7B:
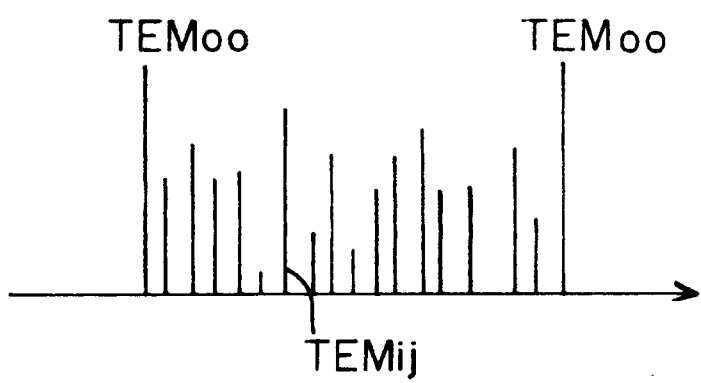
Figure 7C:
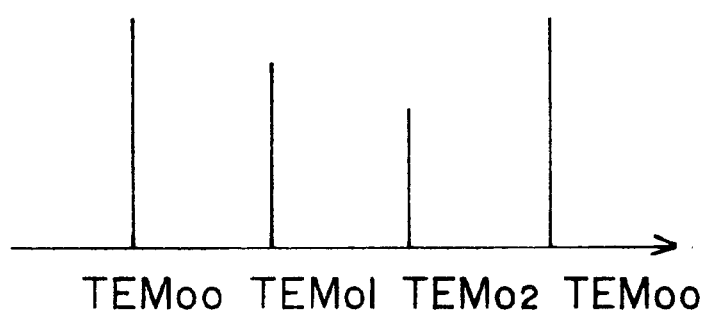
Figure 7D:
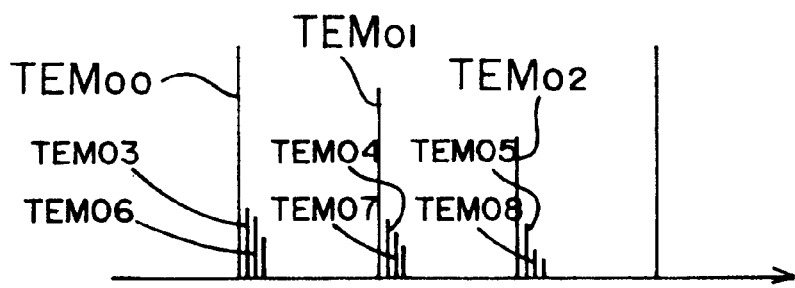

In a known manner, as illustrated in FIGS. 7A to 7D, the positions of the various transverse modes depend on the diameter of the mirrors of a cavity and on the distance between these mirrors. FIG. 7A, which more schematically corresponds to FIG. 3C, only shows main longitudinal modes ($TEM_{00}$) of a cavity. In any case, there is a distribution of the type in FIG. 7B where a very great number of modes $TEM_{ij}$ can appear between two neighboring modes $TEM_{00}$. It is also known, as shown in FIG. 7C, that in the case of a degenerated cavity, that is, a cavity in which the cavity length has a rational relation with the mirror radius, a so-called degenerated mode cavity is obtained, in which most of the modes gather at the same frequencies. Thus, for a cavity with identical mirrors having a length equal to R/2 or 3R/2 (R being the mirror radius), all modes $TEM_{00}$ and $TEM_{ij}$ such that i+j=3n gather at the same frequency, just as $TEM_{01}$ and $TEM_{ij}$ such that i+j=3n+1, and as $TEM_{02}$ and $TEM_{ij}$ such that i+j=3n+2.

The operation in the embodiment of FIG. 7B is not satisfactory since it is not known on which mode the locking will occur. The operation on a degenerated configuration of the type in FIG. 7C is also not satisfactory since several lateral modes will be simultaneously excited each time the laser has locked and their relative intensity is variable.

Thus, according to an aspect of the present invention, it is advocated to use a cavity in a configuration close to a degenerated configuration, in which the minor lateral modes will be gathered in the immediate vicinity and on a same side of a main TEM mode ($TEM_{00}$, $TEM_{01}$, and $TEM_{02}$ in the considered case). Thus, in the context of an implementation of the present invention, when the laser performs its scanning, it will necessary lock on one of the main cavity TEM modes. Then, when it will unlock from this mode (see FIG. 4A), it will be too distant in frequency from one of the immediately neighboring secondary lateral modes and will only be able to lock on one of the next main lateral modes.

Further, the excitation of the secondary lateral modes in the cavity may, in a known manner, be strongly reduced by performing a coupling by adequate optical systems between the laser and the cavity (mode matching).

Of course, the present invention is likely to have various alterations and modifications which will occur to those skilled in the art. In particular, various types of cavities, various control systems, and various analysis systems may be used.

What is claimed is:

1. A method of gas trace detection by a laser coupled to a resonant optical cavity containing a chemical species to be analyzed, characterized in that it includes the steps of:

providing that a coupling between the laser and the cavity is such that a light is only sent back to the laser when the cavity is in a resonance mode and at a resonance frequency;

providing a semiconductor laser of a type adapted to providing an emission amplified and thinned down at a reinjected frequency, and such that, when a current rectangular pulse is applied thereto, its frequency moves from a determined initial frequency to a determined final frequency;

exciting the laser by a first current rectangular pulse so that the laser frequency sequentially locks on successive modes of the cavity;

measuring a fall time of the light intensity in the cavity at an end of said rectangular pulse; and repeating the steps of excitation and measurement for successive current rectangular pulses, to cover a spectral range to be analyzed.

2. The method of claim 1, characterized in that the laser is a laser diode.

3. The method of claim 1, characterized in that the laser is excited by sequential current rectangular pulses of increasing intensity.

4. The method of claim 1, characterized in that the laser is excited by sequential current rectangular pulses of increasing length.

5. The method of claim 1, characterized in that the laser is excited by identical sequential current rectangular pulses, a temperature at which the laser is stabilized being incremented after each rectangular pulse.

6. The method of claim 1, characterized in that the cavity is of V-shaped type, comprised of a first mirror oblique with respect to a direction of incidence of the laser, a second mirror orthogonal to the direction of incidence of the laser, and a third mirror forming a cavity with the first two mirrors.

7. The method of claim 1, characterized in that the cavity is a conventional cavity with two mirrors and a polarizing isolator is arranged between the laser and the cavity to prevent the returning to the laser of a direct reflection on a rear surface of an entrance mirror and to transmit to the laser a radiation having undergone a resonance in the cavity.

8. The method of claim 1, characterized in that the cavity is set to operate in a mode close to a degenerated mode, secondary transverse modes being all gathered on a same side of a main corresponding transverse mode, the laser performing a scanning in a direction starting from a side opposite to that where secondary lateral modes are found.

* * * * *